(12) United States Patent
Schwab et al.

(10) Patent No.: US 6,506,944 B1
(45) Date of Patent: Jan. 14, 2003

(54) PREPARATION OF SUBSTITUTED OLEFINS

(75) Inventors: Peter Schwab, Bad Dürkheim (DE); Michael Schulz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/505,707

(22) Filed: Feb. 17, 2000

(30) Foreign Application Priority Data

Feb. 22, 1999 (DE) .......................... 199 07 519

(51) Int. Cl.⁷ .................. C07C 45/00; C07C 69/00; C07C 281/00; C07C 255/00
(52) U.S. Cl. .................. 568/459; 568/478; 568/480; 560/4; 560/12; 564/37; 558/435
(58) Field of Search ................ 568/420, 459, 568/478, 480; 556/136, 21; 502/155, 156, 158, 169; 562/400; 560/4, 12; 564/37; 558/435

(56) References Cited

U.S. PATENT DOCUMENTS 5,312,940 A * 5/1994 Grubbs et al. .............. 556/136
5,849,851 A * 12/1998 Grubbs et al.

FOREIGN PATENT DOCUMENTS

WO       WO-97/06185 A1 *  2/1997 ............. C08F/4/80

OTHER PUBLICATIONS

Bosma et al, Metathesis of unsaturated nitriles, 1984, Journal of Organometallic Chemistry, 280 (1985) 115–122.*
Chem. Lts. 1019–1024, 1976, Nakamura et al.
J. Org. chem., 280 (1985) 115–122, Bosma et al.
J. Molecular Cat., 76 (1992) 181–187, Bespalova et al.
J.C.S. Chem. Comm., 1981, 1081, Bosma et al.
J Chem. Soc., Chem Comm. 1082, Nikokavouras et al.
J. Chem.Soc. 1983, vanden Aardweg et al. 262–263.
Int.Syp.on Metathesis, Sep. 19–21, 1997, Verkuijlen et al.

* cited by examiner

*Primary Examiner*—Sreeni Padmanabhan
*Assistant Examiner*—Sikarl A. Witherspoon
(74) *Attorney, Agent, or Firm*—Keil & Weinkauf

(57) ABSTRACT

$C_6$ compounds of the formula (I)

$$E-CH_2-CH=CH-CH_2-E^1 \qquad (I)$$

are prepared by self metathesis or cross metathesis of compounds of the formulae (II) and/or (III)

$$R-CH=CH-CH_2-E \qquad (II)$$

$$R^1-CH=CH-CH_2-E^1 \qquad (III)$$

where

E, $E^1$ are independently —CHO, —COOH, —COOR², —C(O)NR³R⁴, —CN,

R, $R^1$ are independently H, $C_{1-12}$-alkyl, $C_{6-12}$-aryl or $C_{7-13}$-alkylaryl and $R^2$, $R^3$, $R^4$ are independently H, $C_{1-12}$-alkyl, $C_{7-13}$-aralkyl, in the presence of a homogeneous catalyst comprising ruthenium compounds or ruthenium complexes.

14 Claims, No Drawings

PREPARATION OF SUBSTITUTED OLEFINS

The present invention relates to a process for preparing substituted olefins by self metathesis or cross metathesis.

Olefin metathesis (disproportionation) involves, in its simplest form, a reversible, metal-catalyzed transalkylidenation of olefins by rupture and reformation of carbon-carbon double bonds. In the case of the metathesis of acyclic olefins, a distinction is made, for example, between a self metathesis in which an olefin is transformed into a mixture of two olefins having different molar masses (for example, conversion of propene into ethene and 2-butene) and cross metathesis or co-metathesis which describes a reaction of two different olefins (for example, reaction of propene with 1-butene to give ethene and 2-pentene). Further application areas of olefin metathesis include syntheses of unsaturated polymers by ring-opening metathesis polymerization (ROMP) of cyclic olefins and acyclic diene metathesis polymerization (ADMET) of α,ω-dienes. Relatively new applications are the selective ring opening of cyclic olefins with acyclic olefins and also ring closure reactions (RCM) by means of which, preferably starting from α,ω-dienes, unsaturated rings of various ring sizes can be prepared.

Catalysts suitable for metathesis reactions are, in principle, homogeneous and heterogeneous transition metal compounds.

Heterogeneous catalysts, for example molybdenum, tungsten or rhenium oxides on inorganic oxidic supports, display high activity and regenerability in reactions of nonfunctionalized olefins, but must frequently be pretreated with an alkylating agent to increase the activity when functionalized olefins such as methyl oleate are used. Olefins containing protic functional groups (for example hydroxyl groups, carboxyl groups or amino groups) lead to spontaneous deactivation of the heterogeneous catalyst.

The present invention concerns a process for preparing bifunctionalized $C_6$-hydrocarbons of the $ECH_2CH=CHCH_2E$ type, for example adipic acid and derivatives thereof, with a metathesis reaction of an olefin of the $RCH=CHCH_2E$ type being carried out as key step for forming the $C_6$ unit.

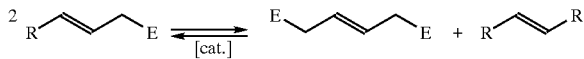

$C_6$-Hydrocarbons of this type are, after functionalization, industrially important precursors and intermediates: adipic acid serves, for example, as precursor for the production of nylon 6.6 (fiber sector) and has hitherto been prepared mostly by oxidative cleavage of cyclohexane. More recent developments involve formative reactions for adipic acid from butadiene, for example by the Monsanto process by carbonylation of the intermediate 1,4-dimethoxy-2-butene and in the BASF process by two-stage carbonylation of butadiene in the presence of methanol.

The two-stage carbonylation requires drastic reaction conditions and gives, starting from butadiene, only quite moderate yields of adipic acid, namely about 70% over the two stages.

The abovementioned metathesis reaction therefore appears to be a possible alternative route to the desired compounds.

The generally high activity of homogeneous metathesis catalysts in respect of olefins is drastically reduced when using electron-depleted olefins such as acrylic acid or their derivatives. In particular, self metathesis reactions of olefins of the $RCH=CH(CH_2)_nE$ type to form $RCH=CHR$ and $E(CH_2)_nCH=CH(CH_2)_nE$ become problematical in the presence of the known metathesis catalysts when E is an electron-withdrawing substituent, n is zero or 1 and R=H, alkyl or aryl. Use of substituted olefins such as methyl 3-pentenoate, 3-pentenoic acid or 3-pentenonitrile in self metathesis reactions is consequently accorded little mention in the literature because of unsatisfactorily low activity.

J. Chem. Soc., Chem. Commun. 1983, 262–263, J. Chem. Soc., Chem. Commun. 1981, 1081–1082 and J. Organomet. Chem. 1985, 280, 115–122, describe the self metathesis of unsaturated nitriles of the $CH_2=CH(CH_2)_nCN$ type in the presence of heterogeneous $Re_2O_7/Al_2O_3$ catalysts which have been activated with $SnMe_4$ or $SnEt_4$. While 4-pentenonitrile is reacted in a yield of up to about 90%, allyl cyanide does not undergo any productive metathesis reactions with the exception of isomerization to form crotononitrile.

Recl. Trav. Chim. Pays-Bas 1977, 96(11), 86–90, describes metathesis reactions of low molecular weight unsaturated esters using the homogeneous catalyst system $WCl_6/SnMe_4$. Although methyl 3-pentenoate is reacted with a selectivity of 95% to form 2-butene and the dehydroadipic ester in the presence of 2 mol % of $WCl_6/SnMe_4$, a disadvantage is the high sensitivity of the catalyst system toward impurities in the feed. Metathesis reactions using unsaturated acids are not possible when the catalyst system mentioned is employed.

J. Mol. Catal. 1992, 76, 181–187, is concerned with the metathesis of functionalized olefins using the catalyst system $WCl_6$ (or $WOCl_4$) /1,1,3,3-tetramethyl-1,3-disilacyclobutane (DSBC). In the best experiment using $WOCl_4$/DSBC, methyl 4-pentenoate is converted with a selectivity of 94% at conversions of 54% into the corresponding $C_8$-diester. In the presence of the same catalyst system, allyl cyanide is converted with a selectivity of 82% at a conversion of 53% into dehydroadipodinitrile with elimination of ethene.

Chem. Lett. 1976, 1021–1024, describes the self metathesis of methyl 4-pentenoate in a conversion of 60% when using $WCl_6/Me_2Al_2Cl_2$.

It is an object of the present invention to develop an economically attractive synthetic route to bifunctionalized $C_6$-hydrocarbons from readily accessible starting materials under moderate reaction conditions using a suitable, generally usable catalyst system.

We have found that this object is achieved by a process for preparing $C_6$ compounds of the formula (I)

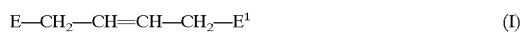  (I)

by self metathesis or cross metathesis of compounds of the formulae (II) and/or (III)

  (II)

  (III)

where

E, $E^1$ are independently —CHO, —COOH, —COOR², —C(O)NR³R⁴, —CN,

R, $R^1$ are independently H, $C_{1-12}$-alkyl, $C_{6-12}$-aryl or $C_{7-13}$-alkylaryl and $R^2$, $R^3$, $R^4$ are independently H, $C_{1-12}$-alkyl, $C_{7-13}$-aralkyl, in the presence of a homogeneous catalyst comprising ruthenium compounds or ruthenium complexes.

Accordingly, the object is achieved according to the present invention by a process sequence in which the key step for forming a $C_6$-hydrocarbon of the $ECH_2CH=CHCH_2E$ type is a self metathesis reaction of an olefin of the $RCH=CHCH_2E$ type according to the following equation:

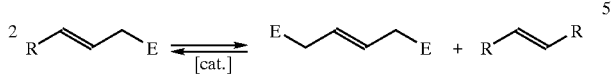

As coproduct, $RCH=CHR$ is formed in stoichiometric amounts and can, if desired, be processed further by subsequent reactions. For example, α-olefins of the $CH_2=CHR$ type can be obtained by ethenolysis of $RCH=CHR$.

In the above equation, E is an aldehyde, ester, acid, acid amide or nitrile function. R is hydrogen or an alkyl, aryl or alkylaryl radical. Preferred alkyl radicals R are linear $C_{1-6}$-alkyl radicals, e.g. methyl or ethyl, or branched $C_{1-6}$-alkyl radicals in which the branching point is at least one methylene group away from the double bond.

It is also possible to react substrates having different radicals R, $R^1$ and E, $E^1$ with one another in a cross metathesis reaction. In this case, mixed reaction products have to be expected.

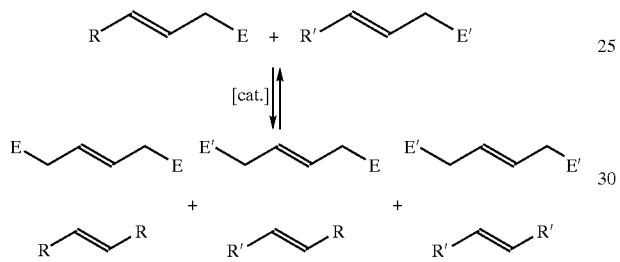

Preferably, E=E' and R=R'. E and E' are particularly preferably ester or carboxyl groups. R and R' are preferably methyl or ethyl groups.

The process of the present invention is carried out in the presence of a homogeneous catalyst comprising ruthenium compounds or ruthenium complexes. Preference is given to using ruthenium-alkylidene complexes as catalyst. The ruthenium-alkylidene complexes are preferably selected from among

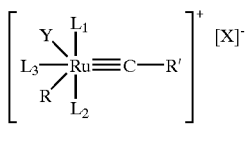
A

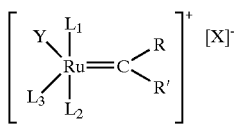
B where
B can be stabilized by a further ligand $L_4$ and
X is an anion which does not coordinate or coordinates only weakly to the metal center,
Y is a monodentate or polydentate anionic ligand,
R and R' are each, independently of one another, hydrogen or a substituted or unsubstituted $C_{1-20}$-alkyl, $C_{6-20}$-aryl or $C_{7-20}$-alkylaryl radical and
$L_1$, $L_2$, $L_3$ and $L_4$ are, independently of one another, uncharged electron donor ligands, or ruthenium complexes of the formulae C or D

$RuX'Y'(=CH—CH_2R'')L^1L^2$ (C)

$RuX'Y'(=CHR'')L^1L^2$ (D)

where
X', Y' are identical or different anionic ligands,
R'' is hydrogen or a substituted or unsubstituted $C_{1-20}$-alkyl radical or $C_{6-20}$-aryl radical, and
$L^1$ and $L^2$ are, independently of one another, uncharged electron donor ligands.

The uncharged electron donor ligands are preferably phosphines, arsines, stibines containing at least two bulky groups, amines, pyridines, π-coordinated olefins or solvent molecules. The uncharged electron donor ligands are particularly preferably selected from among phosphines of the formula $PR^aR^bR^c$ in which $R^a$ and $R^b$ are, independently of one another, phenyl radicals or sterically hindered organic radicals and $R^c$ is hydrogen or a substituted or unsubstituted $C_{1-12}$-alkyl radical or $C_{6-20}$-aryl radical or is as defined for $R^a$.

$R^a$ and $R^b$ are preferably selected from among i-propyl, tert-butyl, cyclopentyl, cyclohexyl, phenyl or menthyl.

Such complexes are described, for example, in WO 93/20111, WO 96/04289, WO 96/06185, WO 97/03096, and also in DE-A-197 36 609 and DE-A-198 00 934.

The cationic catalyst systems comprise as active components cationic ruthenium complexes of the formula A (cationic carbyne complexes) or B (cationic carbene complexes) or mixtures comprising them

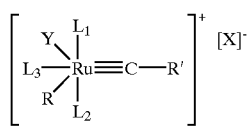
A

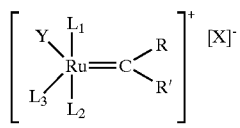
B where B can be stabilized by a further ligand $L_4$.
In the structures A and B,
$X^-$ is an anion which does not coordinate or coordinates only weakly to the metal center, for example a complex anion from main groups III to VII of the Periodic Table of the Elements, e.g. $BR''_4^-$ (R''=F, phenyl which may bear one or more fluorine atoms or perfluorinated $C_{1-6}$-alkyl radicals as substituents, e.g. $C_6H_{5-n}F_n$ where n=1 to 5), $PF_6^-$, $AsF_6^-$, $SbF_6^-$, $ClO_4^-$, $CF_3SO_3^-$ or $FSO_3^-$,
Y is a monodentate or polydentate anionic ligand,
R and R' are each, independently of one another, hydrogen or a substituted or unsubstituted $C_{1-20}$-alkyl, $C_{6-20}$-aryl or $C_{7-20}$-alkylaryl or -aralkyl radical, and
$L_1$, $L_2$, $L_3$ and $L_4$ are, independently of one another, uncharged electron donor ligands, preferably nitrogen donors such as amines and pyridines, phosphines, arsines, stibines containing at least two bulky groups such as i-propyl, t-butyl, cyclopentyl, cyclohexyl, menthyl or the like, or else π-coordinated olefins or solvent molecules.

The radicals preferably have the following meanings:
$X^-$ is $BR''_4^-$ where R'=F or $C_6H_3$ (m-$CF_3$)$_2$, Y is halogen, preferably chlorine, or OR where R=$C_{1-6}$-alkyl, $C_{6-12}$-aryl, preferably phenoxide, R is H, R' is $C_{1-6}$-alkyl, $C_{6-12}$-aryl, $C_{7-20}$-aralkyl, preferably methyl or benzyl, $L_1$, $L_2$ are phosphines containing at least two bulky groups, $L_3$, $L_4$ are cyclic or acyclic ethers or tertiary amines such as $NMe_2phenyl$, $NMe_3$, $NEt_3$.

The synthesis of the active components A and/or B or of mixtures comprising these active components can be carried out starting from numerous organometallic starting materials, for example by reaction of hydrido(vinylidene) complexes of the RuY (H) (=C=CHR)$L_1L_2$ type which can be synthesized by reacting RuClH($H_2$)$L_1L_2$ with terminal alkynes HC≡CR, with $R^+X^-$, where $X^-$ is a noncoordinating or weakly coordinating anion. RuClH($H_2$)$L_2$ can be prepared by literature methods, for example from the polymeric ruthenium precursor [$RuCl_2$(COD)]$_x$ (COD=cyclooctadiene) in i-propanol in the presence of L under a hydrogen atmosphere (Werner et al., Organometallics 1996, 15, 1960 to 1962) or starting from the same starting material in sec-butanol in the presence of L and tertiary amines ($NEt_3$) under a hydrogen atmosphere (Grubbs et al., Organometallics 1997, 16, 3867 to 3869). RuClH($H_2$)$L_2$ can also be obtained starting from $RuCl_3.H_2O$ in THF by reaction with L in the presence of activated magnesium under a hydrogen atmosphere (BASF AG, DE-A-198 00 934 which has earlier priority but is not a prior publication) and is preferably reacted in situ with 1-alkynes to give the corresponding hydrido(chloro)vinylidene complexes RuClH(=C=CHR)$L_2$. The latter can be isolated or reacted in situ with $H^+X^-$ ($X^-$=noncoordinating anion) to give the active components A and/or B used according to the present invention.

By reaction of compounds of the RuYY' (=CHR)$L_1L_2$ type (where Y can be the same as Y') with $R^+X^-$, where $X^-$ is a noncoordinating or weakly coordinating anion. Mixed anionic alkylidene complexes RuXY (=CHCH$_2$R)$L_2$ can be prepared as described in DE-A-198 00 934 starting from RuXH(=C=CHR)$L_2$.

By reaction of compounds of the RuYY'(=CHR)$L_1L_2$ type with anion-abstracting metal salts $M^+X^-$ or Lewis acids such as $BF_3$ or $AlCl_3$ in the presence of a ligand $L_3$, where $X^-$ is a noncoordinating or only weakly coordinating anion and the anionic ligands Y and Y' can be identical or different. MX can, for example, be $AgPF_4$, $AgB(C_5F_5)_4$, $AgPF_6$ or $AgSbF_6$. $R^+X^-$, $M^+X^-$ and the corresponding Lewis acids are preferably used in a molar ratio to the organometallic starting material of from 1:10 to 1000:1.

The reactions to form the active components A and/or B are preferably carried out in organic solvents under an inert gas atmosphere, preferably in solvents which can stabilize an unsaturated metal center by coordination, for example aliphatic or cyclic ethers such as dioxane or THF, amines, DMSO, nitriles, phosphines, arsines, stibines, water, olefins or other two-electron donors. The reaction is preferably carried out in THF at from −100 to +100° C., preferably from −80 to −40° C., and pressures from 1 mbar to 100 bar, preferably from 0.5 to 5 bar.

The reaction can be carried out using one or more molar equivalents of $R^+X^-$. $L_{1-3}RX$ formed when using excess $R^+X^-$ does not have an adverse effect on the reaction. The resulting compositions comprising the active components A and/or B can be used in situ as a highly active metathesis catalyst system or can be stored at low temperatures under an inert gas atmosphere. The active components A or B can, if desired, be used in isolated form.

As a rule, the reaction is complete after from 1 s to 10 h, preferably after from 3 s to 1 h. Suitable reaction vessels are generally glass or steel vessels which may, if desired, be lined with ceramic.

The preparation of the ruthenium complexes of the formula (C)

$$RuX'Y' (=CH—CH_2R")L^1L^2 \qquad (C)$$

where

X', Y' are identical or different anionic ligands,

R" is hydrogen or a substituted or unsubstituted $C_{1-20}$-alkyl radical or $C_{6-20}$-aryl radical and $L^1$ and $L^2$ are, independently of one another, uncharged electron donor ligands, is preferably carried out by (a) reacting $RuX_3$ with $L^1$ and $L^2$ in an inert solvent in the presence of a reducing agent and hydrogen and compounds of the formula IV

$$R"—C≡CH \qquad (IV)$$

where R" is as defined above, in the presence or absence of water, to give a compound of the formula V

$$RuX'H(=C=CHR")L^1L^2 \qquad (V)$$

where X', R", $L^1$, $L^2$ are as defined above, (b) separating the compound of the formula V from the reaction mixture and subsequently reacting it in an inert solvent with HY', ($HL^1$)Y' or ($HL^2$)Y' and compounds of the formula IV

$$R'—C≡CH \qquad (IV)$$

where R" is as defined above, in the presence or absence of water, (c) subsequently reacting the product with HY', [$HL^1$]Y' or [$HL^2$]Y'.

It has been found that the above ruthenium complexes can be obtained in very good yields directly from $RuX'_3$, preferably $RuCl_3.3(H_2O)$, by simple reaction with ligands $L^1$ and $L^2$, hydrogen and terminal alkynes of the formula IV in the presence of reducing agents without isolation of intermediates. These ruthenium complexes have no vinylic substituents on the carbene carbon atom. The starting materials can be prepared inexpensively and are readily available.

To prepare mixed anionic complexes of the formula (C), the intermediate of the formula V is obtained or isolated and subsequently reacted further. This enables different ligands X' and Y' to be introduced.

The first stage of the synthesis is the reaction of $RuX'_3$ with the ligands $L^1$ and $L^2$ in an inert solvent in the presence of a reducing agent and hydrogen. Solvents which can be used are aromatics, heteroaromatics, cyclic or acyclic ethers. Preferred solvents are toluene, NMP, tetrahydrofuran, dialkyl ethers, glycol ethers and dioxane. Particular preference is given to tetrahydrofuran.

As reducing agent, it is possible to use any reducing agent which reduces Ru(III) to Ru(II) under the reaction conditions. The reduction is preferably carried out using hydrogen in the presence of a metallic or nonmetallic reducing agent, preferably in the presence of an alkali metal, an alkaline earth metal or a transition metal such as palladium or zinc which is present in metallic form and/or can be applied to a support. The alkaline earth metals, preferably magnesium, are preferably used in an activated form. The activation can be achieved, for example, by contacting with a chlorine-containing organic solvent. For example, in a single-vessel reaction under an inert gas atmosphere, magnesium can be placed in a diluted chlorine-containing organic solvent, for example dichloroethane, in the reaction vessel and, after an induction period of from one second to 10 hours, preferably from one minute to one hour, reacted with the solvent, $RuX'_3$ and the ligands $L^1$ and $L^2$ under a hydrogen atmosphere. The temperature in this reaction step (a) is preferably from 0 to 100° C., particularly preferably from 20 to 80° C., in particular from 40 to 60° C. The pressure is preferably from 0.1 to 100 bar, particularly preferably from 0.5 to 5 bar, in particular from 0.8 to 1.5 bar. The reaction is carried out for a period of preferably from 10 minutes to 100 hours, particularly preferably from one hour to 10 hours. The molar ratio of ligands $L^1$ and $L^2$ together to the ruthenium salt used is preferably 2–20:1, particularly preferably 2–5:1. After the reaction in step (a), the reaction mixture is preferably at a temperature in the range from –80 to 100° C., particularly preferably from –40 to 50° C., in particular from –30 to 20° C., with a 1-alkyne. Here, the molar ratio of ruthenium salt originally used to 1-alkyne is preferably from 1:1 to 1:10. The reaction is preferably carried out at a pressure of from 0.1 to 10 bar, particularly preferably from 0.8 to 1.5 bar, in particular from 1 to 1.4 bar, for a period of preferably from 30 seconds to 10 hours, particularly preferably from one minute to one hour. In the ruthenium complexes of the formula (C), X' is a monodentate anionic ligand, for example halogen, pseudohalogen, carboxylate, diketonate. X' is particularly preferably halogen, in particular bromine or chlorine, especially chlorine. The reaction is particularly preferably carried out using $RuCl_3 \cdot 3H_2O$.

In the ruthenium complexes of the formula (C), Y' can be the same ligand as X'. It is preferably a halogen different from X' or a carboxyl group bound to a polymer or a support, which makes it possible to fix the catalyst to a support. The ligand X' in the intermediates of the formula V can be replaced by salt metathesis with MY', where M is an alkali metal or ammonium, preferably potassium. This also makes it possible to obtain product mixtures.

$L^1$ and $L^2$ are, as described above, uncharged electron donor ligands. The radical R is hydrogen or a substituted or unsubstituted $C_{1-20}$-, preferably $C_{1-6}$-alkyl radical or $C_{6-20}$-, preferably $C_{6-8}$-aryl radical. Particularly preferred ruthenium complexes of the formula (C) are the complexes $RuCl_2(=CH—CH_3)(PCy_3)_2$ and $RuCl_2(=CH—CH_2—Ph)(PCy_3)_2$, where Cy is a cyclohexyl radical and Ph is a phenyl radical.

The ruthenium complexes of the formula $$RuX'_2(=CH—CH_2R'')L^1L^2$$

where
X' is an anionic ligand,
R'' is hydrogen or a substituted or unsubstituted $C_{1-20}$-alkyl radical or $C_{6-20}$-aryl radical, and
$L^1$ and $L^2$ are, independently of one another, uncharged electron donor ligands, can also be obtained by a) reacting $RuX'_3$ with a diene in a solvent based on one or more aliphatic secondary alcohols in the presence or absence of a reducing aid, and then with $L^1$ and $L^2$ in the presence of at least one coordinating weak base and hydrogen, and, without isolating intermediates, b) subsequently reacting the product with compounds of the formula

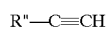

where R'' is as defined above, in the presence of a soluble chloride source.

Compared to the catalyst systems described in the prior art, the ruthenium complexes used according to the present invention enable, inter alia, high selectivities together with comparatively long catalyst operating lives to be achieved even at very low catalyst concentrations (100 ppm—1%) under mild reaction conditions (T=0–200° C., p=1 bar absolute).

When using internal olefins $RCH=CHCH_2E$ in which R=Me or Et, the introduction of ethylene may be necessary or at least helpful for increasing the conversion in accordance with the following equation. In this case, ethylene can be used as stripping gas.

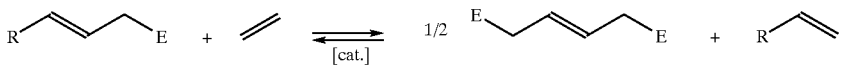

The addition of solvents, for example pentane, acetone, ether and toluene, is not necessary in any of the reactions described, but it has no adverse effect on the reaction either.

The reactions are carried out at from 0 to 200° C. and pressures of from 0.01 to 100 bar and are generally complete after from 10 minutes to 100 hours.

The reactions can be carried out continuously or batchwise in reactors such as glass vessels, reaction tanks, tube reactors or circulation reactors. Since the reactions are equilibrium reactions, it is advantageous to remove the process products from the equilibrium as quickly as possible in order to achieve a very high conversion. This is particularly useful for reactions in which low boilers such as ethene, 2-butene or propene are formed as coproducts.

To isolate the process products, the reaction mixture, which may comprise catalyst dissolved or suspended in the process product, is worked up by distillation and the process product can be isolated after a fine distillation. The catalyst-containing distillation bottoms can be returned to the reaction. The catalyst can also be recycled in a high-boiling solvent. It is also conceivable for the process of the invention to be performed in a reactive distillation apparatus in order to remove low-boiling components formed in situ from the equilibrium so as to maximize the conversion.

The compounds of the $RCH=CHCH_2E$ type (R and E, see above) used as starting materials for the metathesis reaction can be obtained, for example, in high yields from readily available starting materials such as dienes, for example butadiene, by hydroformylation, carbonylation or hydrocyanation.

The further processing of the bifunctionalized $C_6$-hydrocarbons present in the metathesis product can be carried out by, inter alia, hydrogenation, hydroformylation, reductive amination, oxidation or ring closure.

The invention is illustrated by the following examples.

EXAMPLE 1
Synthesis of Methyl Dehydroadipate ($C_6$-diester)

In a Schlenk tube, 100 g (0.88 mol) of methyl 3-pentenoate (3-MP) are reacted with 677 mg (0.9 mmol) of $RuCl_2(=CHMe)(PCy_3)_2$ at various temperatures and atmospheric pressure. Within a few minutes, a characteristic color change of the solution from violet to wine red is observed. The reaction space remains closed during the entire duration of the experiment, so that low-boiling coproducts formed cannot escape. Samples are taken after various reaction times and are analyzed by gas chromatography. The results are summarized in the following tables:

|   | 1 h | 5 h | 20 h |
|---|---|---|---|
| T = 20° C. | | | |
| Conversion$_{3\text{-MP}}$ | 9 | 12 | 18 |
| Selectivity$_{C6\text{-diester}}$ | 100 | 100 | 99 |
| T = 40° C. | | | |
| Conversion$_{3\text{-MP}}$ | 13 | 15 | 18 |
| Selectivity$_{C6\text{-diester}}$ | 99 | 99 | 98 |
| T = 80° C. | | | |
| Conversion$_{3\text{-MP}}$ | 20 | 21 | 2 |
| Selectivity$_{C6\text{-diester}}$ | 99 | 98 | 97 |

EXAMPLE 2
Synthesis of Dehydroadipic Acid ($C_6$-diacid)

In a Schlenk tube, 100 g (1.0 mol) of 3-pentenoic acid are reacted with 760 mg (1.0 mmol) of $RuCl_2(=CHMe)(PCy_3)_2$ at 80° C. and atmospheric pressure. The reaction space remains closed during the entire duration of the experiment, so that low-boiling coproducts formed cannot escape. Within a few minutes, a characteristic color change of the solution from violet to wine red is observed. After 5 hours, the reaction mixture is analyzed by gas chromatography.

Conversion$_{3\text{-}pentenoic\ acid}$=23%
Selectivity$_{c6\text{-}diacid}$=98%

EXAMPLE 3
Synthesis of Methyl Dehydroadipate ($C_6$-diester) in the Presence of Ethylene In a Schlenk tube provided with a gas inlet, 100 g (0.88 mol) of methyl 3-pentenoate are reacted with 677 mg (0.9 mmol) of $RuCl_2(=CHMe)(PCy_3)_2$ at room temperature and a gentle stream of ethylene is passed into the solution. Within a few minutes, a characteristic color change of the solution from violet to wine red is observed. Propylene formed is stripped from the solution for 1 hour by means of the continuing ethylene stream. The reaction mixture is subsequently analyzed by gas chromatography.

Conversion$_{3\text{-}pentenoic\ acid}$=45%
Selectivity$c_{6\text{-}diester}$=98%

EXAMPLE 4
Synthesis of Methyl Dehydroadipate ($C_6$-diester) at 100 mbar

In a round-bottom flask fitted with a dropping funnel, 100 g (0.88 mol) of methyl 3-pentenoate are admixed at 40° C. with 677 mg (0.9 mmol) of $RuCl_2(=CHMe)(PCy_3)_2$, and a further 400 g (3.51 mol) of methyl 3-pentenoate are gradually added over a period of 1 hour at a reduced pressure of 100 mbar to remove 2-butene formed. The reaction mixture is stirred for another 1 hour at 40° C. and is finally worked up by distillation.

Yield$_{c6\text{-}diester}$=211 g (isolated, 56% of theory)

We claim:

1. A process for preparing compounds of the formula (I)

E—CH$_2$—CH=CH—CH$_2$—E$^1$ (I)

by self metathesis or cross metathesis of compounds of the formulae (II) and/or (III)

R—CH=CH—CH$_2$—E (II)

R$^1$—CH=CH—CH$_2$—E$^1$ (III)

where
E,E$^1$ are independently —CHO, —COOH, —COOR$^2$, —C(O)NR$^3$R$^4$, —CN,
R,R$^1$ are independently H, $C_{1\text{-}12}$-alkyl, $C_{6\text{-}12}$-aryl, or $C_{7\text{-}13}$-alkylaryl and
R$^2$, R$^3$, R$^4$ are independently H, $C_{1\text{-}12}$-alkyl, $C_{7\text{-}13}$-aralkyl, in the presence of a homogenous catalyst comprising ruthenium compounds or ruthenium complexes.

2. A process as claimed in claim 1, wherein ruthenium-alkylidene complexes are used as catalyst.

3. A process as claimed in claim 2, wherein the ruthenium-alkylidene complexes are selected from among cationic ruthenium complexes of the formula A or B or mixtures comprising them

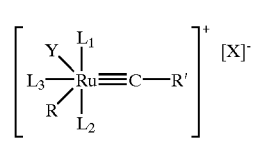

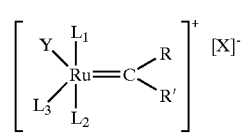

where
B can be stabilized by a further ligand L$_4$ and
X is an anion which does not coordinate or coordinates only weakly to the metal center,
Y is a monodentate or polydentate anionic ligand,
R and R' are each, independently of one another, hydrogen or a substituted or unsubstituted $C_{1\text{-}20}$-alkyl, $C_{6\text{-}20}$-aryl or $C_{7\text{-}20}$-alkylaryl radical and
L$_1$, L$_2$, L$_3$ and L$_4$ are, independently of one another, uncharged electron donor ligands, or
ruthenium complexes of the formulae C or D RuX'Y'(=CH—CH$_2$R")L$^1$L$^2$ (C)

RuX'Y'(=CHR")L$^1$L$^2$ (D)

where
X', Y' are identical or different anionic ligands,
R" is hydrogen or a substituted or unsubstituted $C_{1\text{-}20}$-alkyl radical or $C_{6\text{-}20}$-aryl radical, and
L$^1$ and L$^2$ are, independently of one another, uncharged electron donor ligands.

4. A process as claimed in claim 3, wherein the uncharged electron donor ligands are phosphines, arsines, stibines containing at least two bulky groups, amines, pyridines, π-coordinated olefins or solvent molecules.

5. A process as claimed in claim 4, wherein the uncharged electron donor ligands are selected from among phosphines of the formula $$PR^aR^bR^c$$

where $R^a$ and $R^b$ are, independently of one another, phenyl radicals or sterically hindered organic radicals and $R^c$ is hydrogen, a substituted or unsubstituted $C_{1\text{-}12}$-alkyl radical or $C_{6\text{-}20}$-aryl radical or is as defined for $R^a$.

6. A process as claimed in claim 3, wherein X is halogen and Y is the same halogen or a different halogen or a carboxyl group bound to a polymer or a support.

7. A process as claimed in claim 1, wherein E is identical to E' and R is identical to R'.

8. A process as claimed in claim 1, wherein the reaction is carried out in the presence of ethylene.

9. A process as claimed in claim 1, wherein R—CH=CH—CH$_2$—E is methyl 3-pentenoate or 3-pentenoic acid.

10. A process as claimed in claim 1, wherein a complex of the following formula is used:

$$RuX'_2(=CH—CH_2R'')L^1L^2,$$

where

X' is an anionic ligand,

R'' is hydrogen or a substituted or unsubstituted $C_{1\text{-}20}$-alkyl radical or $C_{6\text{-}20}$-aryl radical, and $L^1$ and $L^2$ are, independently of one another, uncharged electron donor ligands.

11. A process as claimed in claim 10, wherein the following complex is used:

$$RuCl_2(=CH—CH_3)(PCy_3)_2,$$

where

Cy is a cyclohexyl radical.

12. A process for preparing compounds of the formula (I)

$$E—CH_2—CH=CH—CH_2—E' \qquad (I)$$

by self metathesis or cross metathesis of compounds of the formulae (II) and/or (III)

$$R—CH=CH—CH_2—E \qquad (II)$$

$$R^1—CH=CH—CH_2—E^1 \qquad (III)$$

where

E,E$^1$ are independently —CHO, —COOH, —COOR$^2$, —C(O)NR$^3$R$^4$, —CN,

R,R$^1$ are independently H, $C_{1\text{-}2}$-alkyl, $C_{6\text{-}12}$-aryl, or $C_{7\text{-}13}$-alkylaryl and R$^2$, R$^3$, R$^4$ are independently H, $C_{1\text{-}12}$-alkyl, $C_{7\text{-}13}$-aralkyl, in the presence of a homogenous ruthenium-alkylidene complex as catalyst, wherein the ruthenium-alkylidene complex is selected from among cationic ruthenium complexes of the formula A or B or mixtures comprising them

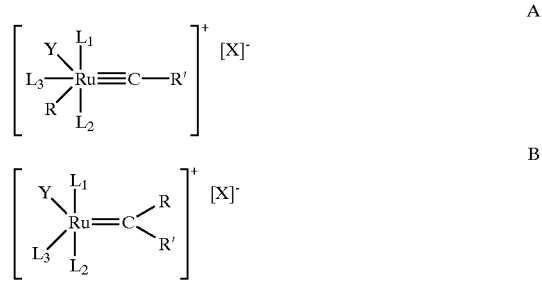

where

B can be stabilized by a further ligand $L_4$ and

X is an anion which does not coordinate or coordinates only weakly to the metal center, Y is a monodentate or polydentate anionic liquid, R and R' are each, independently of one another, hydrogen or a substituted or unsubstituted $C_{1\text{-}20}$-alkyl, $C_{6\text{-}20}$-aryl or $C_{7\text{-}20}$-alkylaryl radical and $L_1$, $L_2$, $L_3$, and $L_4$ are independently of one another, uncharged electron donor ligands.

13. A process for preparing compounds of the formula (I)

$$E—CH_2—CH=CH—CH_2—E^1 \qquad (I)$$

by self metathesis or cross metathesis of compounds of the formulae (II) and/or (III)

$$R—CH=CH—CH_2—E \qquad (II)$$

$$R^1—CH=CH—CH_2—E^1 \qquad (III)$$

where

E,E$^1$ are independently —COOH, —COOR$^2$, —CN,

R,R$^1$ are independently H, $C_{1\text{-}12}$-alkyl, $C_{6\text{-}12}$-aryl, or $C_{7\text{-}13}$-alkylaryl and R$^2$ is H, $C_{1\text{-}12}$-alkyl, $C_{7\text{-}13}$-aralkyl, in the presence of a homogenous catalyst comprising ruthenium compounds or ruthenium complexes.

14. A process as claimed in claim 1, wherein E, E$^1$ in formulae (II) and (III) are —CN.

* * * * *